United States Patent [19]

Tabata

[11] Patent Number: 4,715,384
[45] Date of Patent: * Dec. 29, 1987

[54] PULSIMETER

[75] Inventor: Junichi Tabata, Tokyo, Japan

[73] Assignee: Kabushiki Kaisha Daini Seikosha, Tokyo, Japan

[*] Notice: The portion of the term of this patent subsequent to Apr. 30, 2002 has been disclaimed.

[21] Appl. No.: 463,160

[22] Filed: Feb. 2, 1983

[30] Foreign Application Priority Data

Feb. 3, 1982 [JP] Japan ................................. 57-15660

[51] Int. Cl.⁴ .............................................. A61B 5/02
[52] U.S. Cl. ................................. 128/706; 128/710; 128/687
[58] Field of Search ................... 128/687–689, 128/696, 700, 706, 709–710; 361/212–213

[56] References Cited

U.S. PATENT DOCUMENTS

| | | | |
|---|---|---|---|
| 3,477,421 | 11/1969 | Partridge | 128/709 |
| 3,580,243 | 5/1971 | Johnson | 128/696 |
| 3,742,947 | 7/1973 | Hashem | 128/696 |
| 3,868,948 | 3/1975 | Graetz | 128/709 |
| 4,164,937 | 8/1979 | Spencer | 128/688 X |
| 4,331,158 | 5/1982 | Partridge | 128/709 |
| 4,513,753 | 4/1985 | Tabata et al. | 128/706 |

*Primary Examiner*—William E. Kamm
*Assistant Examiner*—Angela D. Sykes
*Attorney, Agent, or Firm*—Bruce L. Adams; Van C. Wilks

[57] ABSTRACT

A pulsimeter having a detection electrode receptive of electrocardiac signals of a person and a pulse detection circuit, a switching element connected between an input terminal of the pulse detection circuit and a ground level, and a switch for controlling the conduction state and non-conduction state of the switching element so that the detection circuit can be protected from the static electricity by conducting the switching element in the pulse detection mode.

14 Claims, 7 Drawing Figures

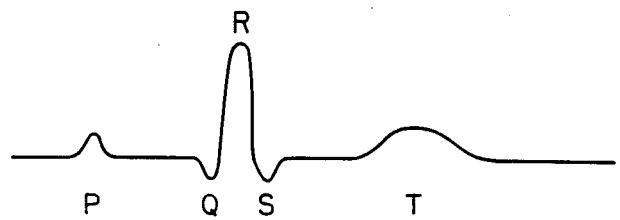
PRIOR ART *FIG. 1*
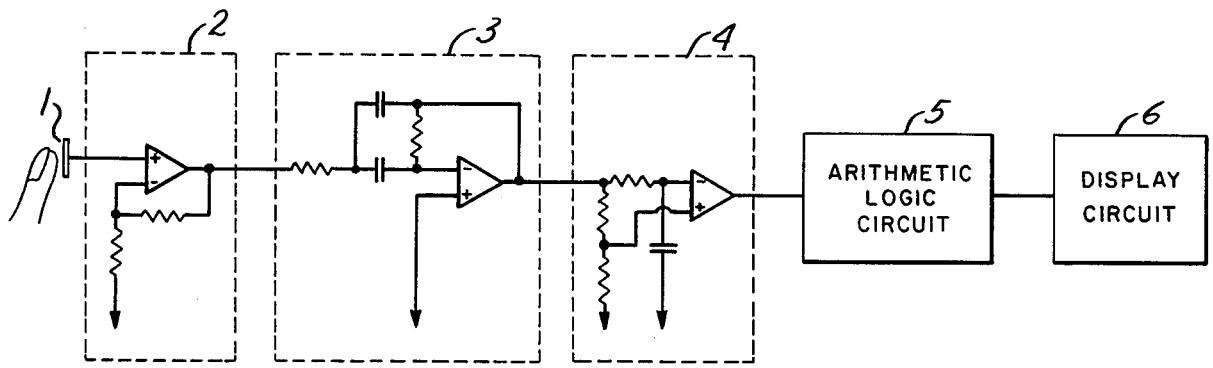
PRIOR ART *FIG. 2*
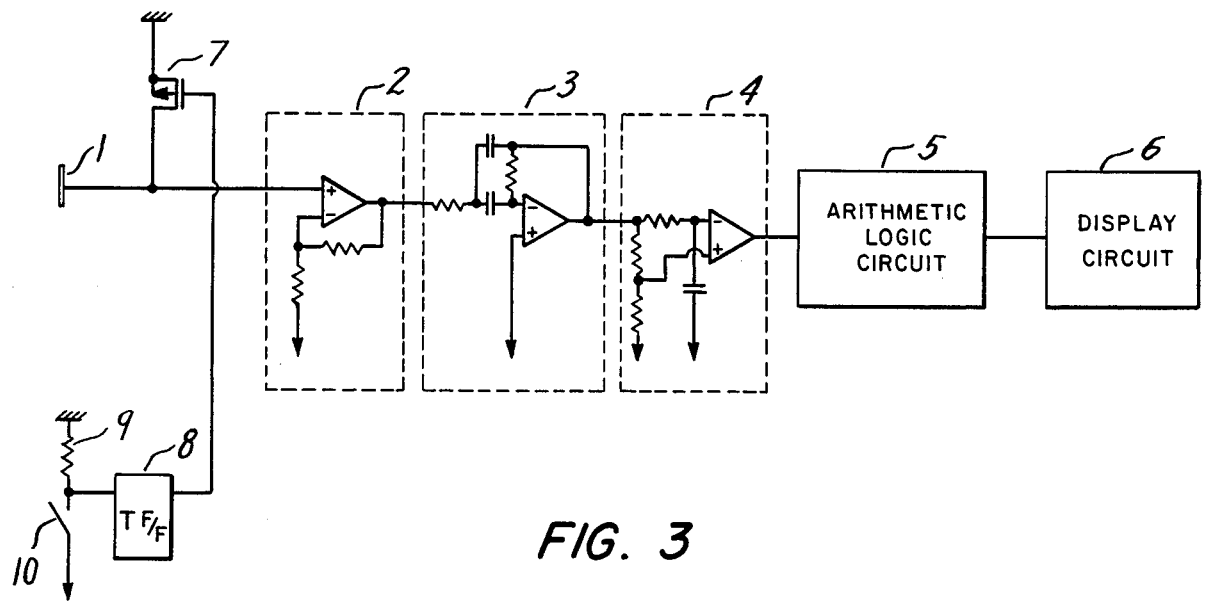
*FIG. 3*

PULSIMETER

BACKGROUND OF THE INVENTION

The present invention relates generally to a pulsimeter, and more particularly to a pulsimeter having a protective circuit for preventing destruction of the pulse detection circuit by static electricity.

Electrocardiography is one of the conventional pulse counting methods. This is the method of detecting minute electric signals from the heart generated before contraction of the heart. The electrocardiography is characterized by the following features:

(1) Simple and highly reliable. Heartbeats can be counted only by touching two metal electrodes with both hands or fingers.

(2) Suitable for miniature devices exhibiting long life. Electric signals from the heart can be detected with minute power (about 100 uW).

A portable miniature pulsimeter can be manufactured using the electrocardiography method. In the conventional circuit and electrode structure, however, the elements of the circuit input portion connected to the electrode may sometimes be destroyed by the electric discharge of static electricity at an instant the person or clothes touches the detection electrode. As a result the pulsimeter may lose the pulse detecting and counting functions.

SUMMARY OF THE INVENTION

It is an object of the present invention to provide a pulse detection circuit with a protective circuit which prevents destruction of the pulse detection circuit by static electricity. It is another object of the invention to provide a highly reliable pulsimeter whose pulse detecting and counting functions are not destroyed by static electricity under any working conditions of the pulsimeter.

BRIEF DESCRIPTION OF THE DRAWINGS

FIG. 1 is a signal waveform of electrocardiography used in the present invention, FIG. 2 is a block diagram of an example of a conventional pulsimeter, FIG. 3 is a block diagram of a pulsimeter according to the present invention.

DESCRIPTION OF THE PREFERRED EMBODIMENTS

Figure 4:
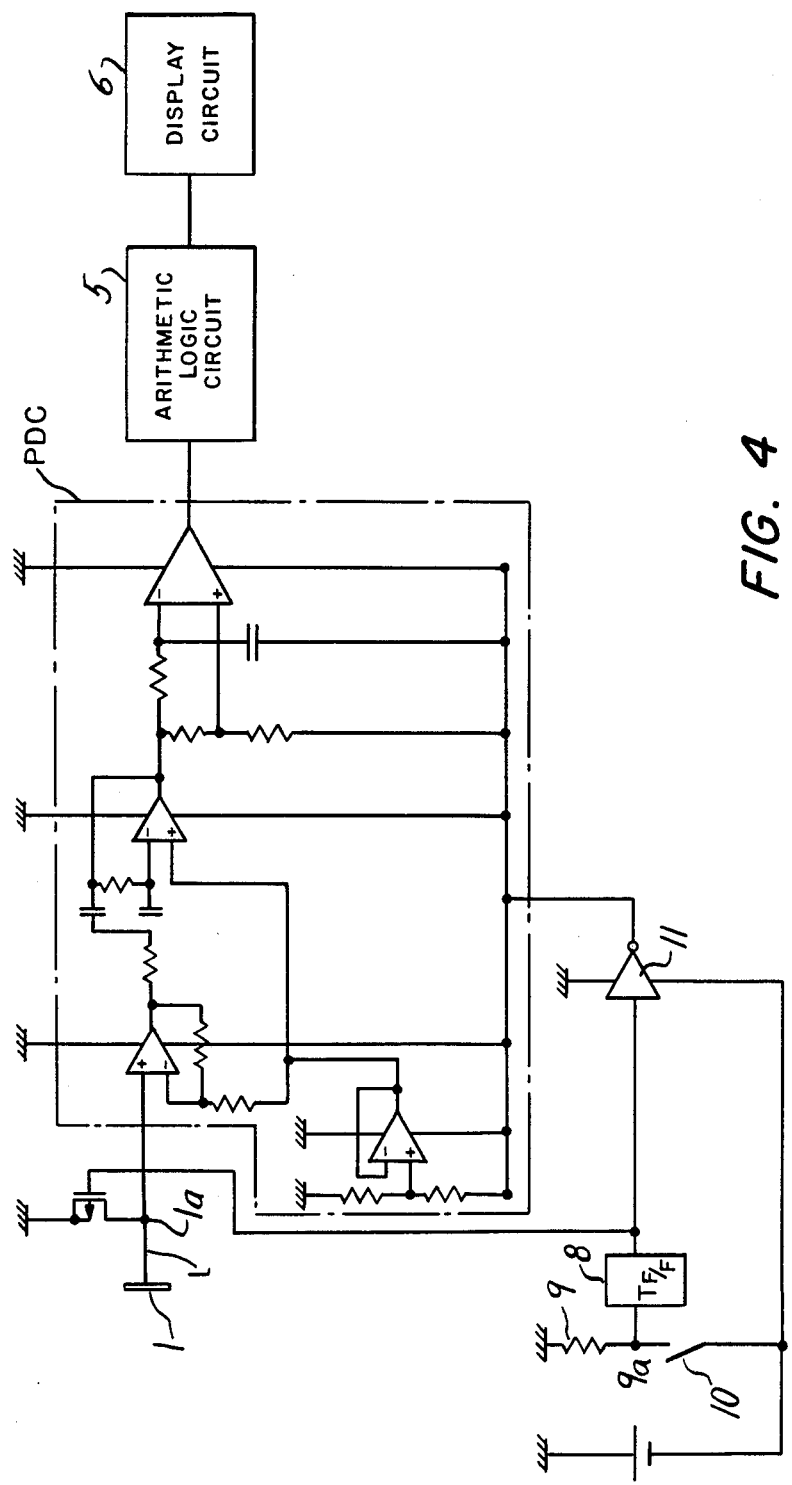
FIG. 4 is a block diagram showing another embodiment of the pulsimeter according to the present invention.

FIG.1 shows a signal waveform produced in electrocardiography and which is used in the present invention.

Generally, electrocardiac potential signals induced between both arms of a person consist of P wave, Q-R-S wave and T wave components which develop periodically. Of these the amplitude of the Q-R-S wave is the largest, i.e., between about 0.2 mV and 1.0 mV. Thus the method of detecting the Q-R-S wave is generally used. Further, electromagnetic noise at the commercial frequency is induced on the skin of the person from the outside and overlaps the electrocardiac potential signal. In counting the pulses, accordingly, it is necessary to eliminate the large noise of the commercial frequency having a large amplitude in order to accomplish sensing the electrocardiac signals having a minute amplitude.

An example of a conventional pulsimeter using electrocardiography is shown in FIG. 2. Reference numeral 1 denotes a detection electrode consisting of a conductor such as stainless or silver chloride. One face of the detection electrode 1 is exposed on the casing surface of a pulsimeter. A pulse is counted by touching the earth or ground of the circuit with a part of the body surface, e.g., a part of the skin of one arm (left arm) and touching the detecting electrode 1 with a part of the skin of the other arm (right arm), e.g., a finger tip. The above counting operation is easily made by connecting the earth of the circuit to the case back of the pulsimeter.

The detection electrode 1 is connected to an amplifying circuit 2. The amplifying circuit 2 can suitably select the amplification factor by combining an operation amplifier with plural resistors.

The electrocardiac potential signal is thus noise amplified to the desired level and fed to a band-pass filter 3. The band-pass filter 3 consists of an operation amplifier, plural resistors and plural capacitors, and the center frequency and Q-valve are selected comparatively freely. The commercial frequency noise is erased by the band-pass filter 3 and only electrocardiac potential signals are produced. The output signals from the band-pass filter 3 are fed to a voltage comparator 4. The voltage comparator 4 detects only the Q-R-S wave and produces pulse signals at an output terminal.

The output pulse signals from the voltage comparator 4 are fed to an arithmetic logic circuit 5. The arithmetic logic circuit 5 counts a period (T sec.) of the input pulse signal and counts the number of pulses per 1 minute. The relationship between the input pulse period (T sec.) and the number of pulses P is given by:

$$P = 60/T$$

Output signals from the arithmetic logic circuit 5 are fed to a display circuit 6 and drives a display comprised of liquid crystal or the like to display the number of pulses.

This electrocardiac potential detection system may save energy by providing a switching circuit for controlling the energy supply from the power source. Namely the switching input is in the OFF state when the pulse is not being counted.

However, a drawback of this prior art construction is that the input transistor of the operation amplifier of the amplifying circuit 2 is apt to be destroyed when the detection electrode 1 on the surface of the pulsimeter receives the static electricity.

For example, static electricity is easily generated in daily life by a person putting on or taking off clothes. The static electricity is discharged as the charged body approaches near the detection electrode 1 both when the pulsimeter is in use or nonuse.

Accordingly the present invention prevents destruction of the detection circuit of the pulsimeter due to static electricity by the following method.

FIG. 3 shows a pulsimeter according to the present invention. Description of the detection electrode 1, the amplifying circuit 2, the band-pass filter 3, the voltage comparator 4, the arithmetic logic circuit 5 and the display circuit 6 are omitted to avoid repetition as these components are the same as those described above with reference to FIG. 2. The present invention is characterized in that an input terminal of the detection circuit is connected to the detection electrode as well as grounded through a switching element. The switching element in this embodiment consists of a P channel MOS FET 7 (referred to as a PMOS 7 hereafter). A source electrode of the PMOS 7 is grounded, a drain electrode of the same is connected to an input terminal of the amplifying circuit 2, and a gate electrode is connected to an output terminal of a T type flipflop 8 (referred to as a T-FF 8 hereafter). An input terminal of the T-FF 8 is connected to a terminal of a resistor 9. The other terminal of the resistor 9 is grounded. One terminal of a mode switch 10 is connected to the input terminal of the T-FF 8 and the other terminal is connected to the negative electrode of the power source. In this embodiment the ground is the positive electrode of the power.

In this circuit structure, an output signal of the T-FF 8 is at "0" level when the pulsimeter is not in use, and the PMOS 7 is in a conductive state. The resistance value of the PMOS in a conductive state is designed to be sufficiently small. The detection electrode 1 is thus effectively grounded. In this state the static electricity discharged to the detection electrode 1 which is exposed to the outside of the pulsimeter flows to the ground through the PMOS 7. Consequently the input portion of the detection circuit is not deteriorated, destroyed or otherwise damaged by the static electricity.

In using the pulsimeter, the user presses the mode switch 10. The mode switch momentarily conducts and returns to the non-conductive state again, resulting in an output signal of the T-FF 8 at logical level "1". In this state the PMOS 7 is in a non-conductive state and the detection electrode 1 is electrically separated from the ground potential. In this condition, the pulsimeter, therefore, is equivalent to FIG. 2 and becomes operable to detect the pulse rate. The user presses the mode switch 10 again on finishing the pulse counting, so that an output signal of the T-FF 8 is at logical level "0" and the P-MOS 7 again conducts. By such a construction the pulsimeter is protected from damage caused by static electricity.

FIG. 4 is a circuit block diagram showing another embodiment of the present invention. A buffer 11 is added in the FIG. 4 embodiment. An input terminal of the buffer 11 is connected to the output terminal of the T-FF 8 and an output terminal thereof is connected to a negative electrode terminal of the pulse detecting circuit. The buffer 11 is an element which performs a logic inverting function. When the pulsimeter is not in use (i.e., the output signal of the T-FF is "0"), the output signal of the buffer 11 is at logic level "1" and the pulse detection circuit does not operate since no current flows in the pulse detection circuit. When the pulsimeter is in use (i.e., the output of the T-FF 8 is "1"), the output signal of the buffer 11 is at logic level "0" and the pulse detection circuit operates. Thus the pulse detection circuit is protected from static electricity and power drain for the whole system is protected by the operation of the mode switch 10.

Figure 5:
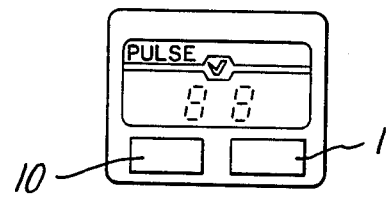
FIG. 5 is a plan view of display device used in the present invention.
Figure 6:
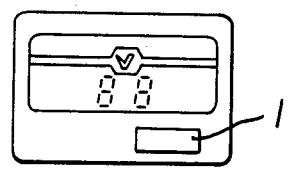
FIG. 6 is a plan view of another display device used in the present invention and, FIG. 7 is a sectional view of a detection electrode and switch used in the present invention.

FIG. 5 and FIG. 6 are plan views of display devices used for the present invention.

Figure 7:
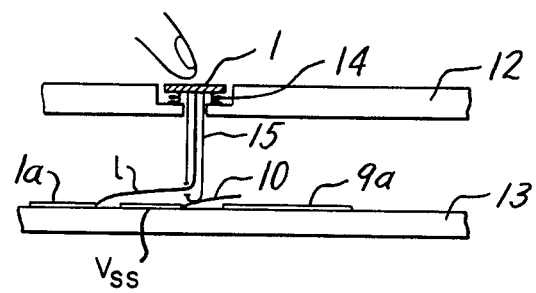

FIG. 7 is a sectional view of detection electrode and switch used for the present invention.

The detection electrode 1 is mounted through springs 14 on the case 12 and is connected though a lead 1 to the input terminal 1a of the pulse detection circuit.

One portion of the lead 1 is molded by an insulating material 15. The mode switch 10 is operated by downward movement of the insulating material 15 in response to actuation of the detection electrode 1, i.e., depression thereof by the finger of the user, and is arranged on the printed circuit board.

The pulsimeter according to the present invention provides a highly reliable pulsimeter having the advantage that the detection electrode can be grounded and the detection circuit can be protected from static electricity. This is achieved by a switching element inserted between the detection electrode and the input terminal of the detection circuit and which connects the detection electrode to ground when the pulsimeter is not in use.

What I claim is:

1. In a pulsimeter having a detection electrode for receiving electrocardiac signals of a person and a pulse detection circuit for processing the electrocardiac signals, the improvement comprising: a switching element connected to the detection electrode and connected between an input terminal of the pulse detection circuit and a ground level; and switch means for controlling the conduction state and non-conduction state of the switching element.

2. A pulsimeter as claimed in claim 1, wherein the switching element is a P channel MOS FET.

3. A pulsimeter as claimed in claim 1, including a memory circuit connected to the switch means for controlling the switching element.

4. A pulsimeter as claimed in claim 1, wherein the pulse detection circuit has operation and non-operation states; and further including a memory circuit for controlling the operation state and non-operation state of the pulse detection circuit.

5. In a heartbeat rate detector of the type having a detection electrode for making contact with a person's skin to detect therefrom electrocardiac signals indicative of the person's heartbeat rate, and circuit means responsive to the electrocardiac signals for detecting therefrom the person's heartbeat rate: circuit protection means connected between the detection electrode and the circuit means for preventing damage to the circuit means caused by the discharge of static electricity to the detection electrode.

6. A heartbeat rate detector according to claim 5; wherein the circuit protection means includes means for discharging the static electricity to ground thereby preventing discharge of the static electricity through the circuit means.

7. A heartbeat rate detector according to claim 5; wherein the circuit protection means includes means for discharging the static electricity to ground before the detection electrode detects electrocardiac signals from the person's skin.

8. A heartbeat rate detector according to claim 7; wherein the means for discharging the static electricity to ground comprises means mounting the detection electrode for manual displacement in response to pressing thereof, and switch means operative in response to manual displacement of the detection electrode to sequentially effect first the discharging of static electricity from the detection electrode to ground followed by the detecting of electrocardiac signals.

9. A heartbeat rate detector according to claim 5; wherein the circuit protection means comprises switching means having a first switching state for effecting the connection of the detection electrode to ground and a second switching state for effecting the connection of the detection electrode to the circuit means, and actuating means for selectively actuating the switching means to the first and second switching states.

10. A heartbeat rate detector according to claim 9; wherein the switching means comprises a semiconductor switching element.

11. A heartbeat rate detector according to claim 10; wherein the semiconductor switching element comprises a MOS FET.

12. A heartbeat rate detector according to claim 9; wherein the actuating means comprises a manually actuatable mode switch.

13. A heartbeat rate detector according to claim 12; wherein the actuating means further comprises means coacting with the mode switch for actuating the switching means to the first and second switching states in accordance with the manual actuation of the mode switch.

14. A heartbeat rate detector according to claim 13; wherein the switching means comprises a semiconductor switching element; and the means coacting with the mode switch comprises a flip-flop having an input connected to the mode switch and an output connected to the semiconductor switching element and operable to change states according to the actuation of the mode switch.

* * * * *